United States Patent [19]

Witiak et al.

[11] Patent Number: 4,542,153
[45] Date of Patent: Sep. 17, 1985

[54] METHODS FOR CHANGING CALCIUM METABOLISM WITHIN THE CELLS OF A MAMMAL

[75] Inventors: Donald T. Witiak, Mount Vernon; Ralf G. Rahwan, Columbus, both of Ohio

[73] Assignee: The Ohio State University Research Foundation, Columbus, Ohio

[21] Appl. No.: 493,601

[22] Filed: May 11, 1983

Related U.S. Application Data

[63] Continuation-in-part of Ser. No. 261,008, May 6, 1981, Pat. No. 4,393,226.

[51] Int. Cl.⁴ .............................................. A61K 31/36
[52] U.S. Cl. ................................................... 514/466
[58] Field of Search ......................... 549/433; 424/282

[56] References Cited

U.S. PATENT DOCUMENTS

| | | | |
|---|---|---|---|
| 2,541,967 | 2/1951 | Kolloff et al. | 260/570.5 |
| 2,916,490 | 12/1959 | Schenck et al. | 260/247 |
| 3,201,470 | 8/1965 | Heubner | 260/577 |
| 3,253,037 | 5/1966 | Huebner | 260/577 |

OTHER PUBLICATIONS

D. T. Witiak, D. R. Williams, S. V. Kakodkar, C. Hite & M. S. Chen, *J. Org. Chem.*, 39, 1242 (1974).
R. G. Rahwan, M. M. Faust & D. T. Witiak, *J. Pharmacol. Exp. Ther.* 201, 126 (1977).
M. F. Piascik, R. G. Rahway & D. T. Witiak, *J. Pharmacol. Exp. Ther.*, 205, 155 (1978).
D. T. Witiak, S. V. Kakodkar, T. P. Johnson, J. R. Baldwin & R. G. Rahway, *J. Med. Chem.*, 22, 77 (1979).
C. E. Akesson, R. G. Rahway, D. T. Witiak, R. J. Brumbaugh, Res. Commun Chem. Pathol, Pharmacol. 27, 265, (1980).
M. F. Piascik, R. G. Rahwan & D. T. Witiak, *J. Pharmacol, Exp. Ther.,* 210, 141 (1979).
M. F. Piascik, M. T. Piascik, D. T. Witiak & R. G. Rahway, *Canad J. Physiol. Pharmacol.,* 57, 1350 (1979).
J. L. Lynch, R. G. Rahway, & D. T. Witiak, *J. Card. Pharmcol.* 60, 49 (1981).

*Primary Examiner*—Ethel G. Love
*Attorney, Agent, or Firm*—Sidney W. Millard

[57] ABSTRACT

2-alkyl-5,6 alkylenedioxyindenes and indane-1-di- or tri-alkylammonium salts are useful as calcium antagonists, for example in arrhythmia. The compounds are prepared from the known corresponding 2,5,6-substituted indene-1-1dimethylammonium salts by alkylation and/or hydrogenation.

24 Claims, 1 Drawing Figure

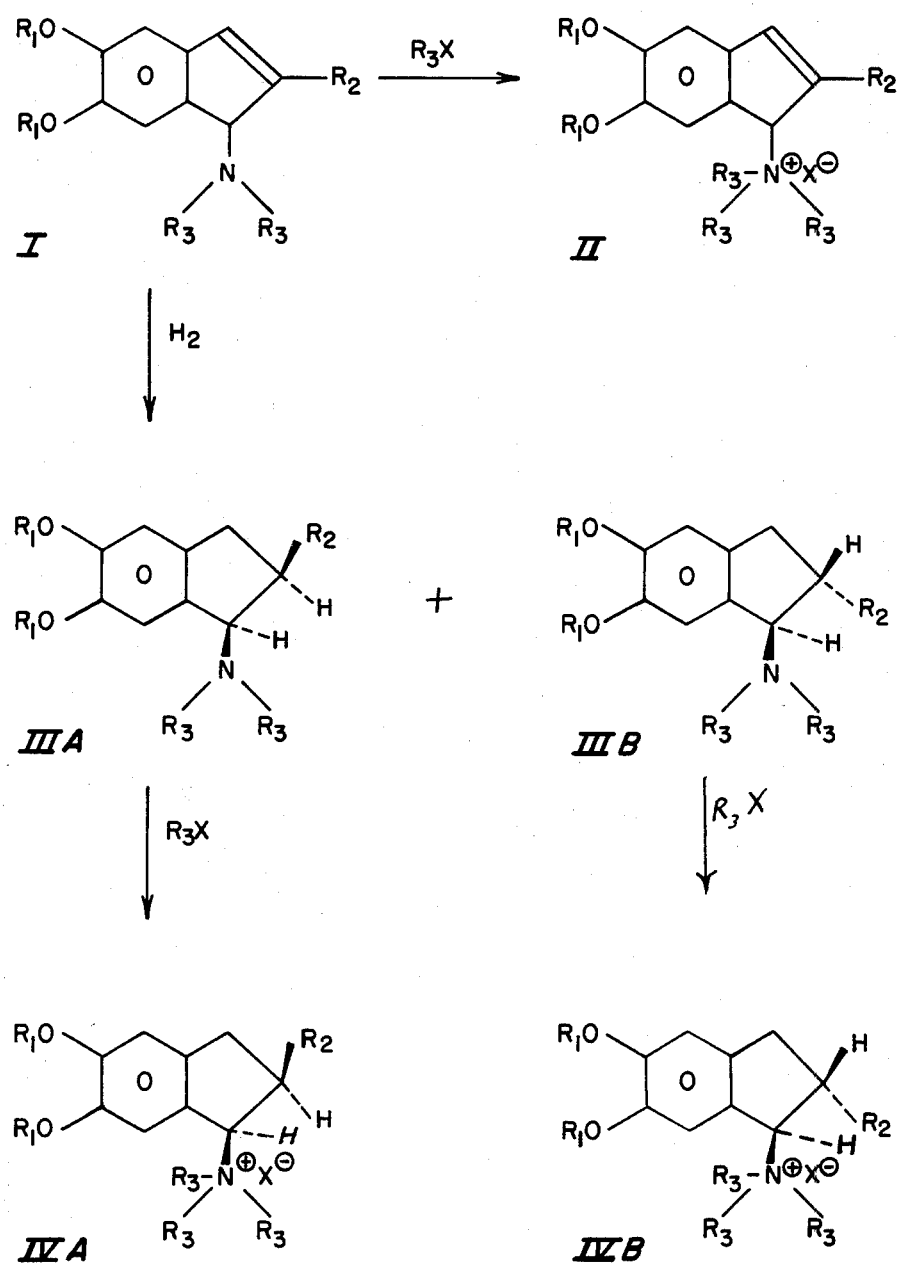

METHODS FOR CHANGING CALCIUM METABOLISM WITHIN THE CELLS OF A MAMMAL

The invention described herein was made in the course of work under a grant #HL 21670 made by the U.S. Department of Health and Human Services.

This application is a continuation-in-part of our co-pending application Ser. No. 261,008 filed May 6, 1981, now U.S. Pat. No. 4,393,226.

BACKGROUND OF THE INVENTION

The invention relates to methods for changing calcium metabolism within the cells of a mammal.

Calcium ions appear to play an important role in innumerable physiological body functions in mammals. Thus, calcium ions are involved in blood clotting and coagulation, cellular adhesion, integrity and membrane stability, bone and teeth formation, enzyme activity, control of certain aspects of cyclic nucleotide metabolism, mediation of certain activities of prostaglandins, cell division, muscle contraction, glandular and other cellular secretory functions, neuronal transmission and numerous other physiological functions. Calcium also effects the pharmacological and toxicological actions of many drugs and chemicals. Accordingly, it is not surprising that the pharmaceutical efficacy of many drugs is dependent at least in part upon their calcium antagonist activity, although in most cases it has only recently been recognized that it is the calcium antagonist activity of the drug which is responsible for its pharmaceutical activity. Such drugs include local anesthetics, anticonvulsants, antiarrhythmics, coronary dilators, antihypertensives and skeletal muscle relaxants as well as other types of drugs.

The calcium required for the aforementioned physiological functions may be derived from either extracellular sources (basement membrane, ground substance or extracellular fluids) or intracellular calcium storage pools (mitochondria, endoplasmic reticulum, nucleus, the inner aspect of the plasma membrane and possibly secretory vesicles). Calcium antagonist drugs may operate either by affecting the rate at which calcium is transported into the cell from extracellular sources or by effecting the metabolism of intracellular calcium (by inhibiting the action or mobilization of intracellular calcium, by enhancing the sequestration of calcium ion by intracellular organelles or by altering its rate of efflux from the cell). The former group of calcium antagonist drugs are known as calcium entry blockers and include local anthestics, manganese, lanthanum, phenytoin, barbiturates, Org 6001 (3α-amino-2β-hydroxy-5α-androstan-17-one), methadone, 1-acetylmethadol, 1-pentazocine, dantrolene, nitroglycerine and other nitrites and organic nitrates, indomethacin, adrenergic $\beta_2$-receptor agonists, morphine, alcohol, aminoglycoside antibiotics such as streptomycin and neomycin, SKF-525A, R33711, flunarizine, cinnarizine, hydralazine, lidoflazine, bepridil, cinepazet maleate, hexoestrol and the prenylamine group of compounds including prenylamine itself, verapamil, methoxyverapamil (D600), fendiline, nifedipine, diltiazem, perhexiline and FR 7534. The physiological action of most of the calcium entry blockers is complicated by the fact that they also block the entry of sodium into the cell and this can make their activity difficult to predict.

The other main group of calcium antagonists which act on intracellular calcium are known as intracellular calcium antagonists and include magnesium, sodium nitroprusside, diazoxide, dantrolene, ryanodine, and the ω-(N,N-diethylamino) alkyl-3,4,5-trimethoxybenzoates.

We have previously synthesized 2-alkyl-5,6-methylenedioxyindene-1-dimethylammonium salts wherein the 2-substituent is an n-propyl or n-butyl group. Although these compounds were obtained as intermediates in the synthesis of potential prostaglandin antagonistic end products, screening of the compounds for potential prostaglandin receptor antagonistic activity on isolated rat uteri showed that these compounds were not selective prostaglandin blockers but indicated that they appear to be calcium antagonists. Our further work on these compounds has indicated that they are indeed intracellular calcium antagonists. In particular, we have shown that these two compounds inhibit rodent nonvascular smooth muscle contraction, bovine coronary vessel constriction and bovine adrenomedullary catecholamine secretion. The compounds have also been shown to increase coronary flow and decrease cardiac inotropic activity in isolated rabbit heart preparations. Moreover, the compounds have been shown to have significant antiarrhythmic activity against ouabain-arrhythmias in dogs, and our further work shows them to be effective against calcium-induced arrhythmias in dogs and rats, and chloroform/anoxia-induced arrhythmias in mice. This further work of ours shows that in the calcium-induced arrhythmia model in rats, both the propyl and butyl compounds were more potent and safer then verapamil, which is one of the standard drugs used in this field. In the chloroform/anoxia-induced arrhythmia model in mice, the butyl compound was more potent than quinidine and the propyl compound was as potent as quinidine. Earlier published work of ours has shown both the propyl and the butyl compounds show a remarkable lack of toxicity when tested acutely and subchronically.

The synthesis and physiological activity of the aforementioned dimethylaminoindenes are described in the following papers:

I. D. T. Witiak, D. R. Williams, S. V. Kakodkar, G. Hite and M. S. Chen, *J. Org. Chem.*, 39, 1242 (1974).

II. R. G. Rahwan, M. M. Faust and D. T. Witiak, *J. Pharmacol. Exp. Ther.*, 201, 126 (1977).

III. M. F. Piascik, R. G. Rahwan and D. T. Witiak, *J. Pharmacol. Exp. Ther.*, 205, 155 (1978).

IV. D. T. Witiak, S. V. Kakodkar, T. P. Johnson, J. R. Baldwin and R. G. Rahwan, *J. Med. Chem.*, 22, 77 (1979).

V. C. E. Akesson, R. G. Rahwan, D. T. Witiak, R. J. Brumbaugh, *Res. Commun. Chem. Pathol. Pharmacol.* 27, 265, (1980).

VI. R. G. Rahwan, M. F. Piascik, D. T. Witiak, *Canad. J. Physiol. Pharmacol*, 57, 443, (1979).

VII. M. F. Piascik, R. G. Rahwan and D. T. Witiak, *J. Pharmacol. Exp. Ther.*, 210, 141 (1979).

VII. M. F. Piascik, M. T. Piascik, D. T. Witiak and R. G. Rahwan, *Canad. J. Physiol. Pharmacol.*, 57, 1350 (1979); and IX. R. G. Rahwan, C. E. Akesson and D. T. Witiak, *Res. Commun. Chem. Pathol. Pharmacol.* 26, 85 (1979).

We have now synthesized derivatives of the aforementioned propyl and butyl aminoindenes and related compounds. Certain of these new derivatives exert a more powerful pharmacological activity than the aforementioned aminoindenes from which they are derived.

SUMMARY OF THE INVENTION

The calcium antagonist compounds of the invention are the compounds of Formulae II, IIIA, and IVA, of the accompanying Reaction Scheme together with the salts of the tertiary amines of Formula IIIA. In each of these formulae $R_2$ is an alkyl group of 1 to about 8 carbon atoms, each $R_3$ independently is an alkyl group of 1 to 3 carbon atoms $X^-$ is an anion, and the two $R_1$ groups together form an alkylene group of 1 to 3 carbon atoms.

Preferably, the two $R_1$ groups together form a methylene group. In all the compounds, $R_2$ is preferably an alkyl group of 2 to about 5 carbon atoms, most preferably 3 or 4 carbon atoms and is desirably n-propyl or n-butyl, each $R_3$ is preferably a methyl group and $X^-$ is preferably a halide ion, most desirably a chloride or iodide ion.

It will be appreciated that the compounds of Formulae IIIA and IVA are cisisomers, while the compounds of Formulae IIIB and IVB are the corresponding transisomers. The invention extends only to the cis isomers.

Specific preferred compounds of Formula II are 2-propyl- and 2-butyl-5,6-methylenedioxyindene-1-trimethylammonium iodides. Specific preferred compounds of Formula IIIA are 2-propyl- and 2-butyl-5,6-methylenedioxyindane-1- dimethylamine and their hydroiodides. Specific preferred compounds of Formula IVA are the cis isomers of 2-propyl- and 2-butyl-5, 6-methylenedioxyindene-1-trimethylammonium iodides.

The invention also provides a method for changing calcium metabolism within the cells of a mammal which comprises administering to the mammal a pharmaceutically-effective amount of a compound of Formula II, IIIA, or IVA or a pharmaceutically-acceptable salt of a compound of Formula IIIA. The mammal may be one suffering from arrhythmia and the pharmaceutically-acceptable amount of the compound administered preferably comprises from about 0.25 to about 10 mg/kg body weight of the mammal. Whereas it is appreciated that only the compound of Formula II was tested in-vivo in mammals and found to have superior antiarrhythmic activity, it is anticipated from the available in-vitro data that compounds of Formulae IIIA and IVA would also exhibit antiarrhythmic activity in-vivo.

It will be noted that the compounds of Formulae II and IVA above are quaternary amines. The pharmaceutical activity of such quaternary compounds demonstrated by our previously-published results set out in papers II and III above suggests that the compounds of Formula I have an intracellular site of action. Since in general ionized compounds do not pass cell membranes, this suggests that the compounds of Formula I reach their intracellular site of action in the non-ionic, free base form. Since no comparable free base form exists for the quarternary compounds of Formulae II and IVA, the quarternary compounds would be expected to be inactive whereas, as shown below, the quaternary compounds are more active than the compounds of Formula I.

Obviously, when one of the instant salts is to be used pharmaceutically, the salt must be one having a pharmaceutically-acceptable anion, for example a halide, nitrate or a sulphate. However, the invention extends to the salts having a non-pharmaceutically-acceptable (i.e. toxic) anion both because such salts are useful in preparing the salts having pharmaceutically-acceptable anions and because the non-pharmaceutically-acceptable salts may represent a more convenient storage form of the compounds than the pharmaceutically-acceptable salts.

BRIEF DESCRIPTION OF THE DRAWING

The accompanying Reaction Scheme shows the reactions employed to produce the compounds of the invention.

DETAILED DESCRIPTION OF THE INVENTION

All the compounds of the invention may be prepared from a 2-alkyl-5, 6-dialkoxyindene-dialkylammonium salt of Formula I (hereinafter, references to 5, 6-dialkoxy compounds should be construed to include both the true 5, 6-dialkoxy compounds, wherein the two R groups are separate alkyl groups, and the 5, 6-alkylenedioxy compounds, in which the two R groups together form an alkylene group). The preparation of some of the compounds of Formula I is described in paper I mentioned above; the mode of preparation of the other compounds of Formula I may be effected by modifications of the process described in that paper which will be obvious to those skilled in the art.

The quaternization of the compounds of Formula I to produce the corresponding compounds of Formula II may be effected by any of the known methods for the quaternization of secondary amines. Conveniently, the quaternization is effected by reaction of the compound of Formula I with the appropriate alkyl halide $R_3X$ to produce the halide salt of Formula II. Conveniently, the reaction is carried out in solution in an alcohol such as absolute ethanol with excess alkyl halide present. If it is desired to prepare a salt of Formula II in which the anion $X^-$ is not a halide, the nonhalide salt may be prepared from the halide salt by simple metathesis.

The hydrogenation of the compounds of Formula I to produce the 2-alkyl-5, 6-dialkoxyindene-1-dialkylamines of Formula IIIA or IIIB and their salts may be effected by any conventional hydrogenation technique but is conveniently effected by passing hydrogen gas through a solution of a compound of Formula I or the corresponding free amine containing a transition metal catalyst such as Raney nickel or finely divided platinum or palladium. The hydrogenation reaction is conveniently carried out in solution in alcohol. It has been found that the hydrogenation reaction produces a major proportion of the cis-isomers of Formula IIIA and only a minor proportion of the trans-isomer of Formula IIIB. The two isomers may be separated by thin layer or column chromatography. If the hydrogenation is effected on a salt of Formula I and it is desired to produce a free amine of Formula IIIA or IIIB, the free amine may of course be liberated from the salt produced simply by the addition of alkali.

For pharmaceutical use, the compounds of Formulae IIIA and IIIB may be in the form of the pure cis or trans-isomer or any mixture of these two isomers.

To prepare a salt of a compound of Formula IIIA or IIIB having an anion different from that of the starting material of Formula I, the anion may be changed by simple metathesis either before or after the hydrogenation reaction.

The quaternization of the compounds of Formulae IIIA and IIIB to produce the 2-alkyl-5,6-dialkoxyindene-1-trialkylammonium salts of Formula IVA or IVB respectively is achieved by the same methods as the quaternization of the compounds of Formula I to produce the compounds of Formula II. Again, if a change of anion is desired, this change may be effected by simple metathesis.

It will be appreciated that the compounds of Formulae IVA and IVB may theoretically be produced by hydrogenation of a compound of Formula II. However, solubility problems in hydrogenating the quaternary compounds of Formula II make it much more convenient to produce the compounds of Formulae IVA and IVB via the compounds of Formulae IIIA and IIIB and their salts.

The compounds of the invention are, as already stated, useful for altering calcium metabolism in mammals. As shown by the animal test results below, compounds of Formula II are substantially more potent in protecting mammals against arrhythmias, in particular chloroform and calcium, induced arrhythmias, than the compounds of Formula I and are less toxic to mammals than the compounds of Formula I.

It should be noted that to secure the proper calcium antagonist activity, the group $R_2$ in each of the active compounds should preferably be an alkyl group of 2 to about 5 carbon atoms, alkyl groups containing 3 to 4 carbon atoms being most efficacious. Compounds having $R_2$ groups outside this range tend to be less pharmaceutically useful.

The following Examples and animal test results are now given, though by way of illustration only, to describe the preparation and pharmaceutical utility of specific preferred compounds of the invention.

EXAMPLE 1

Preparation of
2-butyl-5,6-methylenedioxyindene-1-trimethylammonium iodode

This Example illustrates the preparation of the compound of Formula II in which the two $R_1$ groups together form a methylene group, $R_2$ is n-butyl, each $R_3$ is methyl and $X^-$ is an iodide ion.

50 g. of 3,4-methylenedioxybenzaldehyde (0.33 moles) in 500 ml of ether was reacted with 56.2 g. of n-butyllithium in approximately 360 ml of hexane to produce 68 g (98% of theoretical) of crude 1-(3,4-methylenedioxyphenyl)-pentan-1-ol, which was used in the following step without further purification.

The whole 68 grams of this crude product was fused with 3.5 g. of potassium bisulfate to yield 52 g. (84% of theoretical) of semi-pure 1-(3,4-methylenedioxyphenyl)-pent-1-ene exclusively in the form of the trans-isomer. The semi-pure product, which had already been washed to remove the salt, was used in the following step without further purification.

The whole 52 grams of the semi-pure product was treated with dimethylformamide and phosphorus oxychloride and then, after separation of the intermediate product from the dimethylformamide and the phosphorus oxychloride, with dry hydrogen chloride to yield 2-propyl-5,6-methylenedioxyindene-1-dimethyl ammonium chloride. The yield of pure compound was 25 g., 33% of theoretical; however, using pure olefin yields of approximately 70% are obtained in this reaction.

Except that a different procedure was used in the dehydration step, the above preparation is substantially in accordance with paper I above. 2-Butyl-5,6 methylenedioxyindene-1-dimethylammonium chloride was prepared in precisely the same manner using n-pentyllithium in place of the n-butyllithium in the first step of the process, and 1 g (0.0034 moles) of this hydrochloride was converted to the free base by dissolving the salt in a mixture of 10 ml. of absolute ethanol and 15 ml. of distilled water. The solution was made alkaline with 10% aqueous sodium hydroxide solution and extracted with three 25 ml. aliquots of ether. The combined ether extracts were dried over anhydrous sodium sulfate and the ether was removed under reduced pressure. The oily residue was confirmed as the free amine by its NMR spectrum. The residue was dissolved in 25 ml. of absolute ethanol. 1.5 ml. of methyl iodide was added and the solution was stirred for 24 hours at room temperature. A light yellow solid was separated from the solution by vacuum filtration, washed with absolute ethanol and dried in air to give the crude quaternary iodide. The crude product was recrystallized from a 1:20 ethanol:ether mixture to yield pale yellow needles melting at 150°-151° C. with decomposition and having the expected NMR spectrum showing nine methyl protons.

Elemental analysis yielded the following results: $C_{17}H_{24}NO_2I$. Calculated: C 50.88; H 6.03; N 3.49. Found: C 50.93; H 6.06; N 3.49.

2-propyl-5,6-methylenedioxyindene-1-trimethylammonium iodide may be prepared in the same manner from 2-propyl-5,6-methylenedioxyindene-1-dimethylammonium chloride.

EXAMPLE 2

Preparation of
2-propyl-5,6-methylenedioxyindane-1-dimethylammonium chloride

This Example shows the preparation of a mixture of the compounds of Formulae IIIA and IIIB in which the two $R_1$ groups together form a methylene group, $R_2$ is n-propyl, each $R_3$ is methyl and $X^-$ is a chloride ion, and the separation of the cis and trans-isomers.

1 g. (0.0035 mole) of 2-propyl-5,6-methylenedioxyindene-1-dimethylammonium chloride prepared in Example 1 above was dissolved in 100 ml. of absolute ethanol. A catalytic amount of platinum dioxide was added and this mixture was hydrogenated over a 15 hour period at room temperature and under a hydrogen pressure of 50 lb.in.$^{-2}$. The platinum dioxide catalyst was removed by filtration and the ethanol was removed under reduced pressure to give 1 g. of a crude isomeric mixture. Recrystallization from a mixture of dry ether and absolute ethanol, with addition of charcoal for decolorization, gave 510 mg. (32% of theoretical) of a pure cis product having a melting point of 184°-185° C.

The absence of olefinic protons in the NMR spectrum provided additional evidence that the product was 2-propyl-1-dimethylamino-5,6-methylenedioxyindane hydrochloride. Separation of the cis and trans-isomers from a sample of the crude product was effected by column chromotagraphy on silica gel using ethyl acetate as eluant. The pure cis-isomer isomer exhibited a coupling constant J=2.5 Hz between the protons on $C_1$, and $C_2$, while the trans-isomer had J=7.8 Hz for the same protons (the coupling constants were in both cases measured on the free bases in solution in deuterochloroform). The trans isomer had a melting point of 187°-188° C. and both isomers showed the expected elemental analyses. The reaction proceeded virtually quantitatively, the product being approximately 93% cis and 7% trans.

EXAMPLE 3

Preparation of 2-propyl-5,6-methylenedioxyindane-1-dimethylammonium chloride

This example shows the preparation of a mixture of the compounds of Formulae IIIA and IIIB in which the two $R_1$ groups together form a methylene group, $R_2$ is n-propyl, each $R_3$ is methyl and $X^-$ is a chloride ion, and the separation of the pure cis-isomer.

The compounds were prepared using the same technique as in Example 2 above. 1 g. (0.0035 mole) of 2-butyl-5,6-methylenedioxyindane-1-dimethylammonium chloride prepared in Example 1 above was dissolved in 100 ml of absolute ethanol. A catalytic amount of platinum dioxide was added and the mixture was hydrogenated over a 15 hour period at room temperature and under a hydrogen pressure of 50 lb.in.$^{-2}$. The platinum dioxide catalyst was removed by filtration and the ethanol distilled off under reduced pressure to give 0.95 g. of a viscous oil which solidified on standing. Analysis of this crude product by thin layer chromatography using as solvent a 1:1 mixture of acetonitrile and isopropanol slightly acidified with glacial acetic acid showed the crude product to contain two components (the cis and transisomers of the indane product) and not to be contaminated with indene starting material. Recrystallization of the crude product from a mixture of dry ether and absolute ethanol, with addition of charcoal for decolorization gave 320 mg. (32% of theoretical) of a pure product having a melting point of 184°–185° C. and shown by its NMR coupling constants to be the pure cis-indane.

EXAMPLE 4

Preparation of cis-2-propyl-5,6-methylenedioxyindane-1-trimethylammonium iodide

This example shows the preparation of a compound of Formula IVA in which the two R groups together form a methylene group, $R_2$ is n-propyl, each $R_3$ is methyl and $X^-$ is a iodide ion.

0.65 g. (0.0023 moles) of cis 2-propyl-5,6-methylenedioxyindane-1-trimethylammonium chloride prepared as Example 2 above was converted to the free base with alkali and dissolved in 25 ml. of absolute ethanol. 1.5 ml. of methyl iodide was added and the solution was stirred for 24 hours at room temperature. The ethanol and excess methyl iodide were then removed by distillation under reduced pressure leaving a residue of the crude quaternary iodide. The crude product was recrystallized from a 1:20 ethanol:ether mixture to yield pale yellow needles having the expected NMR spectrum.

Analysis calculated for $C_{16}H_{24}NO_2I\frac{1}{2}H_2O$: C, 48.25; H, 6.47; N, 3.52. Found C, 48.32; H, 6.51; N, 3.46.

ANIMAL TEST RESULTS

Calcium-Induced Arrhythmias

2-Butyl-5,6-methylenedioxyindene-1-trimethylammonium iodide (the compound prepared in Example 1 above and hereinafter abbreviated as Q-bu-MDI) was compared with quinidine, 2-butyl-5-6methylenedioxyindene-1-dimethylammonium hydrochloride (the starting material used in Example 1 and hereinafter abbreviated as bu-MDI), and the corresponding 2-propyl compound (hereinafter abbreviated as pr-MDI) for its effect in protecting against calcium-induced arrhythmias in rats.

The experimental method used was that described in Lynch J. J., Rahwan R. G., Witiak D. T.: Effects of 2-substituted-3-dimethylamino-5,6-methylenedioxyindenes on calcium-induced arrhythmias, *J. Cardiovasc. Pharmacol.* 3: 49–60 (1981). Male Sprague-Dawley rats weighing 180–250 grams were anesthetized with sodium pentobarbital and a cannula was inserted into the left jugular vein for drug administration. Electrocardiograph equipment was connected to the rat and the lead II was continuously monitored. The compound under test, dissolved in 5% dextrose solution, was administered into the jugular vein of anesthetized rats over a 40 second period. Ten minutes after this treatment, an acute dose of 1 ml/kg of a 10% $CaCl_2.2H_2O$ solution was injected into the jugular vein over a period of 10 seconds. The arrhythmias resulting from the calcium administration were graded according to the following criteria: (a) initial change in heart rate following calcium administration; (b) incidences of sinoatrial block, atrioventricular block, ectopic beats, and ventricular flutter and fibrillation; (c) time required for reversion to control ECG; and (d) incidence of mortality.

In controls to which no protective agent was administered, the acute dose of calcium chloride elicited arrhythmias. Within 30 seconds of the calcium administration profound bradycardia occurred. Complex arrhythmias, comprising predominantly sinoatrial block, second and third degree atrioventricular block, nodal and ventricular ectopic beats and ventricular flutter and fibrillation, occurred in 95% of the control animals during and after the initial bradycardia, causing mortality of 30% of the controls. The mean time for reversion to control electrocardiogram in surviving animals was $332 \pm 57$ seconds.

The Q-bu-MDI at a concentration of 0.5 mg/kg afforded partial protection against the calcium-induced bradycardia, almost complete protection against arrhythmia and complete protection against calcium-induced mortality, and also significantly reduced the time for reversion to a normal electrocardiogram. At this dosage, Q-bu-MDI reduced the mortality rate to zero and exhibited no substantial deleterious side effects.

Pr-MDI and bu-MDI were also effective in protecting the rats against calcium-induced arrhythmias without deleterious side effects, but only at a concentration of 3.75 mg/kg. Quinidine produced even worse results than pr-MDI and bu-MDI, being effective only at a concentration of 8 mg/kg. However, at this minimum effective concentration of 8 mg/kg, quinidine severely deepened the S wave. Thus, in this test, Q-bu-MDI was 7–8 times as effective in suppressing arrhythimias as pr-MDI and bu-MDI.

Chloroform Anoxia Assay

The same four compounds were tested for their ability to protect mice from chloroform anoxia by the classical chloroform inhalation procedure described in Lawson J. W.: Antiarrhythmic activity of some isoquinoline derivatives determined by a rapid screening procedure in the mouse, *J. Pharmacol. Exp. Ther.* 160: 22–31, (1968). In this method, chloroform inhalation leading to respiratory arrest produces ventricular fibrillation. Female Swiss albino mice procured from Laboratory Supply Company, Indianapolis, Indiana, weighing 16–22 g, were pretreated intraperitoneally with the compound under test dissolved in a 5% dextrose solution 10 minutes before exposure to chloroform in a closed container containing chloroform-saturated cotton. The mice were removed from the chloroform atmosphere immediately after respiratory arrest and the electrocardiograph lead II monitored. The ED 50 and 95% confidence limits calculated for the anti-arrhythmic agents by the standard method of Litchfield and Wilcoxon.

The ED 50's were:
Q-bu-MDI 10.5 mg/kg
bu-MDI 44 mg/kg
quinidine 67 mg/kg
pr-MDI 68 mg/kg.

Slope functions and tests for parallelism of anti-arrhythmic dose-response curves indicated that the regression lines for the three indenes were parallel to that of quinidine ($p < 0.05$) and that the ED 50 of Q-bu-MDI was significantly smaller than that of quinidine $p << 0.05$).

Toxicity Tests

The LD intraperitoneal 50's of the four compounds tested above and verapamil were tested in mice by the method set out in Paper IX above or similar standard procedures, the experimental values obtained being:
Q-bu-MDI 65 mg/kg
bu-MDI 185 mg/kg
pr-MDI 185 mg/kg
quinidine 225 mg/kg
verapamil 68 mg/kg.

Comparing the LD 50's of the first four compounds mentioned above with the corresponding ED 50's obtained in the chloroform anoxia tests described above, the therapeutic indices of the compounds are shown in the following table:

chloride, 0.29 g/l of magnesium sulphite heptahydrate, 0.3 g/l of calcium chloride dihydrate, 0.16 g/l of potassium dihydrogen phosphate, 2.1 g/l of sodium bicarbonate and 2.1 g/l of dextrose. The contractile force generated by the isolated artria was recorded isometrically under a 500 mg. preload using a Narco Biosystems force transducer connected to a physiograph DMP-4B recorder, both the transducer and the recorder being obtained from E & M Instrument Co. of Houston, Texas.

The isolated left atria were electrically driven by square wave impulses of 3 milliseconds duration at a frequency of 3 Hz. and a voltage of twice the threshold voltage, delivered by a Grass S9 stimulator obtained from Grass Instrument Co., of Quincy, Massachusetts. Two platinum electrodes were used for the stimulation, the anode being in direct contact with the atrial tissue while the cathode had the form of a ring suspended 2.5 centimeters above the anode. Before redetermination of the threshold voltage and generation of a predrug (control) frequency-force profile over the range of 1–5 Hz., an equilibration time of one hour was allowed. The system was then re-equilibrated at 3 Hz. and twice the threshold voltage as before, then one cumulative dose-response curve of contractile force for one test compound was obtained, followed immediately by redetermination of the threshold voltage and the generation of a post-drug frequency-force profile. The sustained peak effect for a given concentration of test compound, in the range of $10^{-8}$M to $3 \times 10^{-4}$M was observed within 3–5 minutes of addition of the test compound to the organ bath. The mean times for generation of the entire dose-response for each of the test compounds, including the generation of predrug and post drug frequency-of force profiles were bu-MDI, $55.0 \pm 3.9$ minutes, Q-bu-MDI $56.9 \pm 1.5$ minutes and pr-MDI $60.8 \pm 4.2$ minutes.

|  | n[a] | ED$_{50}$[b] (mg/kg, i.p.) | LD$_{50}$[b] (mg/kg, i.p.) | Therapeutic Index (LD$_{50}$/ED$_{50}$) | Antiarrhythmic Potency |
|---|---|---|---|---|---|
| Quinidine | 40 | 67.0 (53.3–84.2) | 225 (210–241) | 3.1 | 1.00 |
| Pr—MDI | 40 | 68.0 (52.3–83.4) | 185 (171.3–199.8) | 2.7 | 0.99 |
| Bu—MDI | 40 | 44.0 (34.1–56.7) | 185 (171.3–199.8) | 4.2 | 1.52 |
| Q—bu—MDI | 40 | 10.5 (4.0–27.9) | 65 (56.8–74.4) | 6.2 | 6.38 |

[a]Number of pretreated mice exposed to chloroform.
[b]Mean values and 95% confidence limits.

Thus, Q-bu-MDI is greatly superior to the known compounds quinidine, pr-MDI and bu-MDI as an antiarrhythmic agent.

Effects on Isolated Guinea Pig Atria

The effects of pr-MDI, bu-MDI and Q-bu-MDI on the mechanical and electrical behavior of isolated guinea pig atria were investigated by the method of H. Nawrath, *J. Pharmacol. Exp. Ther.*, 16, 176–182 (1980). The compounds were investigated over the concentration range of $10^{-8}$ to $3 \times 10^{-4}$ M.

English short-haired guinea pigs, supplied by Carr Animal Supply, of Powell, Ohio, weighing 300–600 g. were killed by a blow on the head and both atria of the animal were quickly dissected out and suspended in a water-jacketed organ bath containing Krebs-Henseleit solution through which a 95% oxygen/5% carbon dioxide mixture was bubbled at 32° C. The solution contained 6.92 g/l of sodium chloride, 0.35 g/l of potassium Spontaneously beating right atria were tested in a similar manner. After a one-hour equilibration time, one cumulative dose response curve of rate and contractile force for one test compound was obtained, sustained peak effects for a given concentration of test compound within the range of $10^{-8}$M to $3 \times 10^{-4}$M was observed within 2–3 minutes of addition of the test compound to the organ bath, except that at the highest concentrations of the tertiary test compounds ($10^{-4}$M and $3 \times 10^{-4}$M), particularly in the case of tertiary butyl compound, which required 5–10 minutes to display sustained peak effects. The mean times for generation of the entire dose-response curve for each of the test compounds were bu-MDI $30.9 \pm 2.4$, Qu-MDI $32.7 \pm 1.2$ and pr-MDI $32.0 \pm 3.9$ minutes.

A paired Student's t-test was used to compare pre-drug and postdrug threshold voltages for each left atrial preparations as well as to compare developed tension at each frequency in the profile of each left atrial preparation. P values of less than 0.05 were considered statistically significant.

The dose-dependent decrease in the contractile force of the electrically stimulated left atrium caused by Q-bu-MDI was very modest and never exceeded about 20% at $10^{-4}$M, and this modest-negative inotropic effect was partially reversed at $3\times 10^{-4}$M. Q-bu-MDI also displayed minimal effects on the contractile force of right atria except at $3\times 10^{-4}$M where positive inotropy was found. Even at the maximum concentration of $3\times 10^{-4}$M, Q-bu-MDI did not produce any persistent effects; both the frequency-force relation of the stimulated left atrium and the threshold voltage required to drive this atrium reverted to their normal, pre-testing values soon after administration of the compound. Q-bu-MDI caused only a slight decrease in the spontaneous atrial rate.

The effect of bu-MDI on the dose-dependent decrease in the contractile force of the stimulated left atrium was considerably greater than that of Q-bu-MDI. The much greater negative inotropy of bu-MDI was also brought out by its effects on the non-stimulated right atrium. At $3\times 10^{-4}$M, bu-MDI produced a significant depression of the frequency-force profile of the stimulated left atrium, depressing the tension developed at all frequencies of stimulation and thus rendering the atrium less able to follow high frequency stimulation. At the same concentration, bu-MDI significantly decreased the threshold voltage required to drive the atria. The effect of bu-MDI on the spontaneous atrial rate was substantially identical to that of Q-bu-MDI.

The effects of pr-MDI were generally similar to those of bu-MDI; in particular the effect of the propyl compound on the frequency-force relationship of the left atrium was virtually identical to that of the butyl homolog.

Thus, the effect of Q-bu-MDI upon the electrical and mechanical activity of guinea pig atria is much smaller than that of bu-MDI or pr-MDI. Q-bu-MDI decreases the spontaneous atrial rate and the stimulated atrial force of contraction much less than the other two compounds and has no significant effect upon the threshold voltage for stimulation of the atrium or the frequency-force relation thereof.

In as much as decreases in the contractive force generated by the atrium are deleterious to a mammal being treated with the drug, because such decreases in contractive force tend to cause congestive heart failure and coronary steal phenomena, the above tests indicate that Q-bu-MDI would have less side effects upon the heart than pr-MDI or bu-MDI.

Vasodilator Activity

Pr-MDI, bu-MDI, Q-bu-MDI and the compounds of Formulae IIIA, IIIB and IVA having the two $R_1$ groups together forming a methylene group, each $R_3$ a methyl group and $R_2$ an n-propyl group or n-butyl group (the compounds of Formula III are hereinafter abbreviated as sat-pr-MDI and sat-bu-MDI respectively, reference being made where necessary to the cis isomer of Formula III A or the trans isomer of Formula III B while the compounds of Formula IV are similarly referred to as cis sat-Q-pr-MDI and cis sat-Q-bu-MDI) were tested for vasodilator activity by the method of R. F. Furchgott and S. Bhadrakom, *J. P. Pharmacol. Ex. Ther.*, 108, 129–143 (1953).

The vasodilator activity tests were conducted on male Sprague-Dawley rats, obtained from Harlan Industries, Inc., Cumberland, Indiana. The rats, weight 250–300 g., were sacrified by cervical dislocation and a 2.5 cm. segment of the thoracic aorta was removed and rinshed in physiological buffer. Each aortic segment was cleaned of connective tissue and cut spirally two yield to strips, each 3 by 15 mm. Each strip was mounted isometrically under a tension of 1 g in a 10 ml. tissue bath thermostatically maintained at 37° C. and containing a normal physiological solution aerated with a 95% oxygen/5% carbon dioxide mixture. Forces generated by the strip were monitored using a Grass FT03 isometric transducer coupled to a Grass module 7D polygraph recorder, both the transducer and the recorder being obtained from Grass Instrument Co., of Quincy, Mass.

After the aortic tissue had been allowed to equilibriate for 1–1.5 hours in the normal physiologic solution, tissue contraction was induced by introducing either $10^{-7}$M norepinephrine or 40mM potassium chloride buffer to the tissue bath. Under these conditions, both norepinephrine and potassium chloride introduce a tissue contraction which generates its maximum tension within 30 minutes and which is maintained for many hours. The spasmolytic activity of each test compound was assessed by adding it in increasing concentrations to the solution bathing the aortic tissue and monitoring the resultant tissue relaxation until the maximum relaxation was achieved or a period of 30 minutes had elapsed. The test compound was then washed out of the aortic tissue until the control response to norepinephrine or potassium chloride had been regained.

The results of these experiments are expressed by dividing the tissue tension at each concentration of test compound by the control tension generated by norepinephrine or potassium chloride prior to addition of the test compounds, and expressed in percent. To avoid interference by loss of tension due to time dependent tissue fatigue, separate preliminary experiments were performed to determine the degree of tissue relaxation due to such fatigue and the value of the control tension generated by norepinephrine or potassium chloride prior to the addition of the test compounds was adjusted whenever the duration of the experiment was such that fatigue could be expected to cause more than a 6% loss of tension. The control tensions generated by norepinephrine and potassium chloride were $0.98\pm 0.03$ g. and $0.89\pm 0.05$ g. respectively, these values representing 85.1 and 84.2% respectively of the maximum inducible contractions by these reagents. All concentrations mentioned hereinafter represent the final concentration of the test compound after dilution in the tissue bath.

The figures of concentration against percent response data obtained from each aortic tissue were transformed to its appropriate probit value and $IC_{50}$ values were then estimated using linear regression analysis. The normal physiological solution contained 6.9 g/l of sodium chloride, 0.35 g/l of potassium chloride, 0.11 g/l of magnesium chloride hexahydrate, 0.138 g/l of sodium dihydrogen phosphate, 2.1 g/l of sodium bicarbonate, 0.01 g/l of EDTA, 0.368 g/l of calcium chloride dihydrate and 2.0 g/l of dextrose. The high potassium buffers were obtained by substituting potassium chloride for sodium chloride on an equimolar basis to maintain tonicity.

The $IC_{50}$ values of the test compounds are shown in the following Table (all test compounds have the two $R_1$ groups together forming a methylene bridge and the $R_3$ groups methyl.) to an active form which is responsible for the high activity in vivo.

| Compound # | IC$_{50}$ (mean and range of SEM)M | |
|---|---|---|
| | Norepinephrine | KCl |
| pr—MDI (Formula I, $R_2$ = propyl) | $7.82 \times 10^{-5}(6.66 \times 10^{-5} - 9.19 \times 10^{-5})$ | $2.14 \times 10^{-5}(1.95 \times 10^{-5} - 2.34 \times 10^{-5})$ |
| bu—MDI (Formula I, $R_2$ = butyl) | $7.41 \times 10^{-5}(3.77 \times 10^{-5} - 1.46 \times 10^{-4})$ | $2.03 \times 10^{-5}(1.62 \times 10^{-5} - 2.55 \times 10^{-5})$ |
| Q—bu—MDI (Formula II, $R_2$ = butyl $X^-$ = iodide) | $1.28 \times 10^{-4}(1.02 \times 10^{-4} - 1.61 \times 10^{-4})$ | $1.69 \times 10^{-4}(1.54 \times 10^{-4} - 1.85 \times 10^{-4})$ |
| Q—pr—MDI (Formula II, $R_2$ = propyl, $X^-$ = iodide) | $3.82 \times 10^{-4}(.40 \times 10^{-4} - 4.20 \times 10^{-4})$ | $5.47 \times 10^{-4}(5.13 \times 10^{-4} - 5.84 \times 10^{-4})$ |
| cis sat—pr—MDI (Formula IIIA $R_2$ = propyl) | $5.94 \times 10^{-5}(4.94 \times 10^{-5} - 7.10 \times 10^{-5})$ | $3.00 \times 10^{-5}(2.89 \times 10^{-5} - 3.11 \times 10^{-5})$ |
| trans sat—pr—MDI (Formula IIIB, $R_2$ = propyl) | $3.83 \times 10^{-4}(3.22 \times 10^{-4} - 4.56 \times 10^{-4})$ | $9.89 \times 10^{-5}(9.23 \times 10^{-5} - 1.06 \times 10^{-4})$ |
| cis sat—bu—MDI (Formula IIIA, $R_2$ = butyl) | $3.79 \times 10^{-5}(3.22 \times 10^{-5} - 4.43 \times 10^{-5})$ | $1.74 \times 10^{-5}(1.58 \times 10^{-5} - 1.91 \times 10^{-5})$ |
| trans sat—bu—MDI Formula IIIB, $R_2$ = butyl) | $1.51 \times 10^{-4} - 1.73 \times 10^{-4})$ | $3.11 \times 10^{-5}(2.85 \times 10^{-5} - 3.41 \times 10^{-5})$ |
| cis sat—Q—pr—MDI (Formula IVA, $R_2$ = propyl, $X^-$ = iodide | $1.02 \times 10^{-3}(9.10 \times 10^{-4} - 1.15 \times 10^{-3})$ | $8.71 \times 10^{-4}(6.98 \times 10^{-4} - 1.09 \times 10^{-3})$ |
| cis sat—Q—bu—MDI (Formula IVA, $R_2$ = butyl, $X^-$ = iodide) | $2.81 \times 10^{-4}(2.52 \times 10^{-4} - 3.12 \times 10^{-4})$ | $1.75 \times 10^{-4}(1.67 \times 10^{-4} - 1.84 \times 10^{-4})$ |

The above results show that pr-MDI, bu-MDI, Q-pr-MDI and Q-bu-MDI all relaxed the aortic tissue. In the norepinephrine-treated tissue (which is recognized by those skilled in the art as a more physiologically realistic model of tissue in vivo since people suffering from heart disease tend to have high norepinephrine levels), pr-MDI was considerably more active than Q-pr-MDI. Similarly bu-MDI appears to be considerably more active than Q-bu-MDI. The results obtained with the potassium-chloride-tested tissue are substantially the same as those obtained with the norepinephrine-treated tissue.

Thus, the results of the above tests show that in vivo Q-bu-MDI of Formula II is several times as effective as the tertiary compounds of Formula I. Although the exact ratio of activity between Q-bu-MDI and bu-MDI varies depending upon the exact test being applied, on average Q-bu-MDI is about four times as effective as its tertiary analog and has a higher therapeutic index. Q-bu-MDI is also more potent then quinidine which is used medically as a anti-arrhythmic agent. Since pr-MDI and bu-MDI are the most effective calcium antagonists of Formula I so far produced the degree of anti-arrhythmic activity exhibited by Q-bu-MDI is surprisingly great, especially in view of the relatively small chemical change involved in converting bu-MDI to Q-bu-MDI. Furthermore, since the in vitro tests described above show the Q-bu-MDI and Q-pr-MDI to be less active in vitro than their tertiary analogs, the mode of disposition of the quanternary compounds of Formula II must differ from that of the tertiary compounds of Formula I; it would appear that the compounds of Formula II must be metabolized within the animal body to an active form which is responsible for the high activity in vivo.

The results described above also show that on norepinephrine treated tissue the cis saturated propyl compound of Formula IIIA has substantially the same activity as the corresponding unsaturated propyl compound of Formula I (pr-MDI) mentioned Table I), but the cis saturated propyl compound has a slightly lower activity on potassium chloride treated tissue. The cis saturated butyl compound of Formula IIIA appears to have greater activity on norepinephrine treated tissue than the corresponding butyl compound of Formula I (bu-MDI), while on potassium chloride treated tissue the two compounds have substantially the same activity. However, in all cases the trans isomers of Formula IIIB have markedly lower activity than the corresponding compounds of Formula I on both norepinephrine and potassium chloride treated tissue. The trans isomers of Formula IIIB were also markedly less active than the corresponding cis isomers of Formula IIIA on both types of tissue. Prior to the present invention, those skilled in the art would not have been able to predict the effect of hydrogenating the double bond in the compounds of Formula I and certainly would have had no basis for predicting whether the cis or trans isomers of Formula IIIA and IIIB respectively would be more or less effective than the compounds of Formula I.

The IC$_{50}$ values given also show that in vitro the activity of the propyl and butyl cis isomers of Formula IVA is less than that of the corresponding tertiary compounds of Formula IIIA and of the corresponding compounds of Formula I. Accordingly, in these tests the effect of quarternizing the compounds of Formula IIIA to produce the compounds of Formula IVA appears to produce substantially the same type of effects as quarternizing the compounds of Formula I to produce the compounds of Formula II.

On the basis of the similarity of the action of the instant compounds to the known compounds bu-MDI and pr-MDI, it is believed that in addition to being useful for the treatment of arrhythmia, the instant compounds will also be useful for the treatment of hypertension, for coronary dilation (for example as anti-angina pectoris agents).

We claim:

1. A method for treating a mammal having a condition selected from the group consisting of arrhythmia, hypertension, constriction of the coronary artery and angina pectoris, which method comprises administering to said mammal from about 0.25 to about 10 mg/kg. body weight of said mammal of a pharmaceutically acceptable 2-alkyl-5,6-dialkoxy-indene-1-trialkylammonium salt of the Formula II

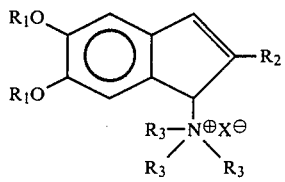

wherein the two $R_1$ groups together form an alkylene group of 1 to 3 carbon atoms, $R_2$ is an alkyl group of 1 to about 8 carbon atoms, each $R_3$ independently is an alkyl group of 1 to 3 carbon atoms and X is an anion.

2. A method according to claim 1 wherein said salt is one in which $R_2$ is an alkyl group of 2 to about 5 carbon atoms.

3. A method according to claim 2 wherein said salt is a 2-propyl- or 2-butyl-5,6-methylenedioxyindene-1-trimethylammonium salt.

4. A method according to claim 3 wherein said salt is an iodide.

5. A method according to claim 1 wherein said mammal is suffering from arrhythmia.

6. A method according to claim 1 wherein said mammal is suffering from hypertension.

7. A method according to claim 1 wherein said mammal is suffering from constriction of the coronary artery.

8. A method according to claim 7 wherein said mammal is suffering from angina pectoris.

9. A method for treating a mammal having a condition selected from the group consisting of arrhythmia, hypertension, constriction of the coronary artery and angina pectoris, which method comprises administering to said mammal from about 0.25 to about 10 mg/kg. body weight of said mammal of a cis 2-alkyl-5,6-dialkoxy-1-dialkylaminoindane of the formula

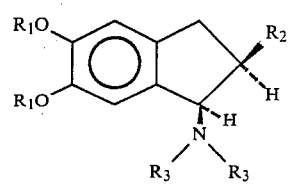

wherein the two $R_1$ groups together form an alkylene group of 1 to 3 carbon atoms, $R_2$ is an alkyl group of 1 to about 8 carbon atoms and each $R_3$ independently is an alkyl group of 1 to 3 carbon atoms.

10. A method according to claim 9 wherein said compound is one in which $R_2$ is an alkyl group of 2 to about 5 carbon atoms.

11. A method according to claim 10 wherein said compound is a 2-propyl- or 2-butyl-5,6-methylenedioxy-1-dimethylammonium salt.

12. A method according to claim 11 wherein said salt is a chloride.

13. A method according to claim 9 wherein said mammal is suffering from arrhythmia.

14. A method according to claim 9 wherein said mammal is suffering from hypertension.

15. A method according to claim 9 wherein said mammal is suffering from constriction of the coronary artery.

16. A method according to claim 15 wherein said mammal is suffering from angina pectoris.

17. A method for treating a mammal having a condition selected from the group consisting of arrhythmia, hypertension, constriction of the coronary artery and angina pectoris, which method comprises administering to said mammal from about 0.25 to about 10 mg/kg. body weight of said mammal of a cis 2-alkyl-5,6-dialkoxyindane-1-trialkylammonium salt of the Formula

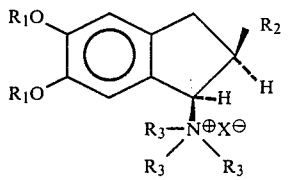

wherein the two $R_1$ groups together form an alkylene group of 1 to 3 carbon atoms, $R_2$ is an alkyl group of 1 to about 8 carbon atoms, each $R_3$ independently is an alkyl group of 1 to 3 carbon atoms and $X^-$ is a pharmaceutically-acceptable anion.

18. A method according to claim 17 wherein said salt is one in which $R_2$ is an alkyl group of 2 to 5 carbon atoms.

19. A method according to claim 18 wherein said salt is a 2-propyl- or 2-butyl-5,6-methylenedioxyindane-1-trimethylammonium salt.

20. A method according to claim 19 wherein said salt is an iodide.

21. A method according to claim 17 wherein said mammal is suffering from arrhythmia.

22. A method according to claim 17 wherein said mammal is suffering from hypertension.

23. A method according to claim 17 wherein said mammal is suffering from constriction of the coronary artery.

24. A method according to claim 23 wherein said mammal is suffering from angina pectoris.

* * * * *